(12) United States Patent
Slack et al.

(10) Patent No.: US 8,651,116 B2
(45) Date of Patent: Feb. 18, 2014

(54) DENTAL FLOSSING MATERIAL WITH MONOFILAMENT THREADER

(76) Inventors: Adrian Harold Sambrooke Slack, Sippy Downs (AU); Maria Elizabeth Slack, Sippy Downs (AU)

(*) Notice: Subject to any disclaimer, the term of this patent is extended or adjusted under 35 U.S.C. 154(b) by 0 days.

(21) Appl. No.: 13/390,384

(22) PCT Filed: Aug. 20, 2010

(86) PCT No.: PCT/AU2010/001068
§ 371 (c)(1),
(2), (4) Date: Feb. 14, 2012

(87) PCT Pub. No.: WO2011/022760
PCT Pub. Date: Mar. 3, 2011

(65) Prior Publication Data
US 2012/0145181 A1 Jun. 14, 2012

(30) Foreign Application Priority Data
Aug. 26, 2009 (AU) .................. 2009904053
Sep. 28, 2009 (AU) .................. 2009904695

(51) Int. Cl.
*A45D 24/00* (2006.01)
*A61C 15/00* (2006.01)

(52) U.S. Cl.
USPC ............ 132/200; 132/321; 132/323; 132/329

(58) Field of Classification Search
USPC ............ 132/321–329, 320, 200, 309; 223/99, 223/102; 433/148, 149, 39; 606/148, 150, 606/225; 112/224, 225; D28/65, 66, 68
See application file for complete search history.

(56) References Cited

U.S. PATENT DOCUMENTS

| | | | | |
|---|---|---|---|---|
| 3,650,392 A * | 3/1972 | Haagedoorn | ............... | 206/369 |
| 3,929,144 A * | 12/1975 | Tarrson et al. | ............... | 132/323 |
| 4,011,658 A * | 3/1977 | Tarrson et al. | ............... | 433/216 |
| 4,064,883 A * | 12/1977 | Oldham | ............... | 132/321 |
| 4,133,339 A * | 1/1979 | Naslund | ............... | 132/323 |
| 4,215,478 A * | 8/1980 | Thomas et al. | ............... | 433/25 |
| 4,330,014 A * | 5/1982 | Glass et al. | ............... | 132/321 |
| 4,832,063 A * | 5/1989 | Smole | ............... | 132/329 |
| 5,183,063 A * | 2/1993 | Ringle et al. | ............... | 132/321 |
| 5,184,631 A * | 2/1993 | Ikeda | ............... | 132/323 |
| 5,289,836 A * | 3/1994 | Peng | ............... | 132/329 |
| 5,311,890 A | 5/1994 | Thornton | | |
| 5,320,117 A | 6/1994 | Lazzara et al. | | |
| 5,353,820 A | 10/1994 | Suhonen et al. | | |
| 5,692,530 A * | 12/1997 | Bible et al. | ............... | 132/321 |
| 5,799,673 A * | 9/1998 | Amendola et al. | ............... | 132/321 |
| 5,970,992 A * | 10/1999 | Anderson | ............... | 132/323 |
| 6,003,525 A * | 12/1999 | Katz | ............... | 132/321 |
| 6,340,027 B1 * | 1/2002 | Hagne et al. | ............... | 132/321 |

(Continued)

FOREIGN PATENT DOCUMENTS

JP   63300756 A   12/1988

*Primary Examiner* — Vanitha Elgart
(74) *Attorney, Agent, or Firm* — Dinsmore & Shohl LLP

(57) ABSTRACT

The present invention relates to a dental cleaning aid. The aid includes a threader (or leader) including a monofilament. A follower is provided for following the threader and the follower is at least in part wider than the monofilament. Preferably, the aid includes a loop or fold fastening arrangement by which the threader and follower are fastened together. In one embodiment, the arrangement includes a fold or loop of the follower engaged with a fold or loop of the threader.

10 Claims, 5 Drawing Sheets

(56) References Cited

U.S. PATENT DOCUMENTS

| | | |
|---|---|---|
| 6,814,086 B2 | 11/2004 | Stallings |
| 8,061,372 B1* | 11/2011 | Allen .............................. 132/329 |
| 8,177,553 B2* | 5/2012 | Stoll ................................ 433/39 |
| 2002/0023659 A1* | 2/2002 | Netto et al. ................... 132/321 |
| 2002/0074012 A1* | 6/2002 | Marcon et al. ................. 132/321 |
| 2006/0207628 A1* | 9/2006 | Millis ........................... 132/321 |
| 2006/0225764 A1 | 10/2006 | Mark |
| 2010/0192972 A1* | 8/2010 | Kazes ........................... 132/322 |
| 2011/0226279 A1* | 9/2011 | Thorne ......................... 132/323 |
| 2012/0222698 A1* | 9/2012 | Fontana et al. ............... 132/321 |

\* cited by examiner

DENTAL FLOSSING MATERIAL WITH MONOFILAMENT THREADER

TECHNICAL FIELD

The present invention relates to a dental cleaning aid and a method for forming a dental cleaning aid.

BACKGROUND

The reference to any prior art in this specification is not, and should not be taken as an acknowledgement or any form of suggestion that the prior art forms part of the common general knowledge.

Dental floss is a bundle of thin nylon filaments or a plastic (teflon or polyethylene) ribbon used to remove food and dental plaque from teeth. The floss is gently inserted between the teeth and scraped along the teeth sides, especially close to the gums.

A dental implant is an artificial tooth root replacement and is used in prosthetic dentistry to support restorations that resemble a tooth or group of teeth. A common type of implant includes posts embedded in a patient's jaw bone. A bridge bearing artificial teeth is then supported by the posts. The gaps between the posts, known in the art as interproximal spaces, can be relatively large when compared with the spacing between teeth, and prone to accumulate food particles, debris, and plaque.

The main reason for dental prosthesis failure is poor oral hygiene. Plaque and calculus are irritants which lead to gum infection. Gingivitis (gum infection) and periodontitis (bone infection) can develop around implants as well as around natural teeth, leading to implant loss as well as tooth loss. In implants this is referred to as peri-mucositis and peri-implantitis. Poor oral hygiene can cause periodontitis as well as decay around natural teeth which support bridges. Decay may lead to the loss of a tooth supporting the bridge.

Dental implants and dental bridges are expensive. Whilst it is important to clean dental implants to ensure that they do not fail, narrow dental floss is not well suited to cleaning the wide gaps between the posts. U.S. Pat. No. 5,320,117 discloses a dental cleaning aid having a comparatively wide strip of cleaning material. The strip defines a narrow threader for initially inserting into gaps and a wide follower which can be reciprocated in the gaps during cleaning. In practice, the material threader may not be resilient enough or be too bulky to be pushed through tight or small inter-dental spaces.

Embodiments of the invention provide a dental cleaning aid with improved threading capabilities.

SUMMARY OF THE INVENTION

According to one aspect of the present invention, there is provided a dental cleaning aid including:
 a threader (or leader) including a monofilament; and
 a follower for following the threader and being at least in part wider than the monofilament, the follower including a folded and twisted length of material.

The dental cleaning aid may include a loop or fold fastening arrangement by which the threader and follower are fastened relative to each other.

A leading portion of the threader may be fine to facilitate threading though gaps whereas a trailing portion of the follower may be wide to facilitate cleaning in the gaps.

The threader may define a loop through which the follower passes. Preferably, the monofilament is a single strand of nylon or other polymeric material fastened relative to itself to form the loop. Alternatively, the threader is injection molded from thermoplastic material as a single piece. The leading portion of the threader consisting of the doubled over monofilament is comparatively narrow and resistant to bending to facilitate threading through gaps.

The follower may be resiliently stretchable. The follower may be able to be stretched to about 1.4 times its resting length. The follower may be able to be stretched to be of comparable width as a leading portion of the threader. The material may be a multi-strand nylon yarn.

The nylon yarn may be texturized nylon 6.0 or 6.6 yarn. The nylon yarn may consist of six plies of a 300 denier (333 dtex) texturized nylon yarn. The yarn may have 68 filaments per ply. The final strand may be 1800 denier (2000 dtex) with a filament count of 408.

The follower material may be a soft gauze-like material. The material may be non-woven or woven, including cotton, viscose wood pulp or polymeric fiber. The material may be moisture-absorbent and impregnated with flavored particles or an antibacterial agent.

According to another aspect of the present invention, there is provided a dental cleaning aid including:
 a threader; and
 a follower for following the threader and including a folded and twisted length of material.

According to another aspect of the present invention, there is provided a method for forming a dental cleaning aid, the method involving the step of fastening a threader, including a monofilament, relative to a follower being at least in part wider than the monofilament, the fastening involving twisting the follower to contain the threader within the follower.

The method may further include the step of applying to the follower one or more of a wax, flavorants, colourants, and an antibacterial agent.

The step of fastening may involve fastening the threader to itself to form a loop through which the follower passes.

According to another aspect of the present invention, there is provided a method for forming a dental cleaning aid, the method involving the step of twisting a follower to contain a threader within the follower.

The method may further include the step of applying to the follower one or more of a wax, flavorants, colourants, and an antibacterial agent.

The method may further include the step of fastening the threader to itself to form a loop through which the follower passes.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows.

DETAILED DESCRIPTION OF PREFERRED EMBODIMENTS

Figure 1:
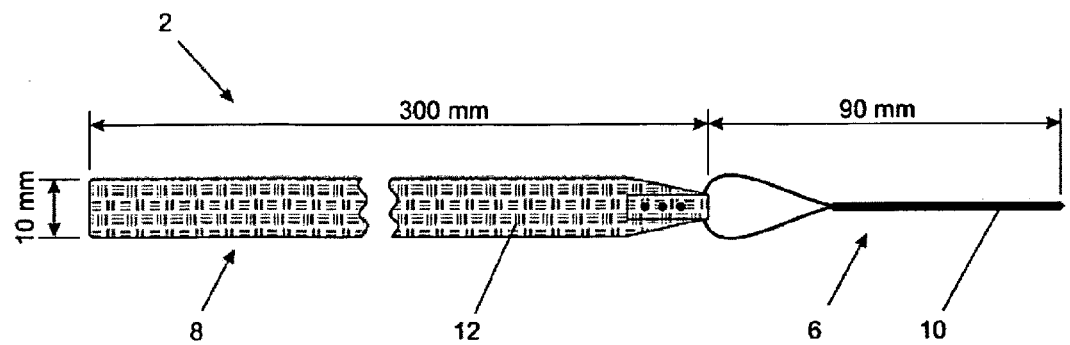
FIG. 1 is a plan view of a dental cleaning aid in accordance with an embodiment of the present invention.
Figure 2:
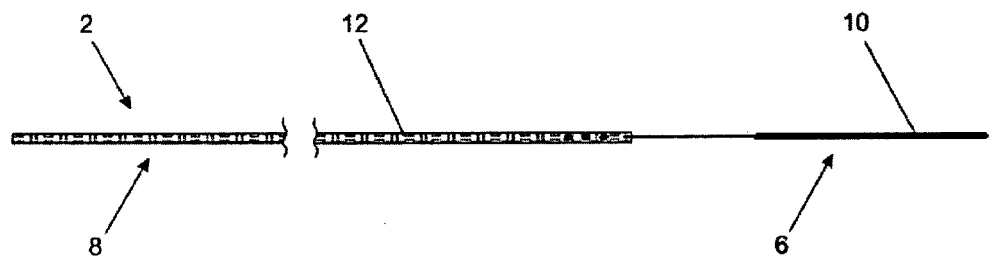
FIG. 2 is a side view of the dental cleaning aid of FIG. 1.
Figure 3:
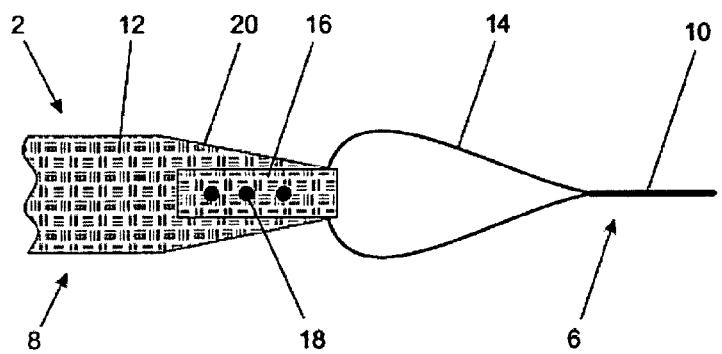
FIG. 3 is a close up view of a loop fastening arrangement of the dental cleaning aid of FIG. 1.
Figure 4:
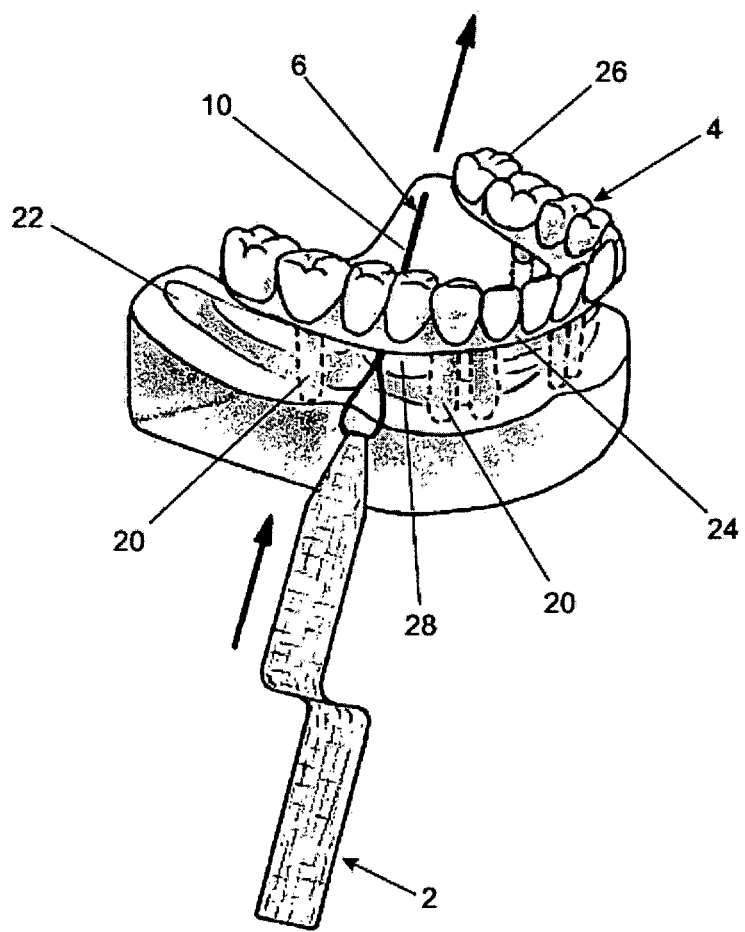
FIG. 4 shows a threader of the dental cleaning aid of FIG. 1 being threaded through a gap of a dental prosthesis.
Figure 5:
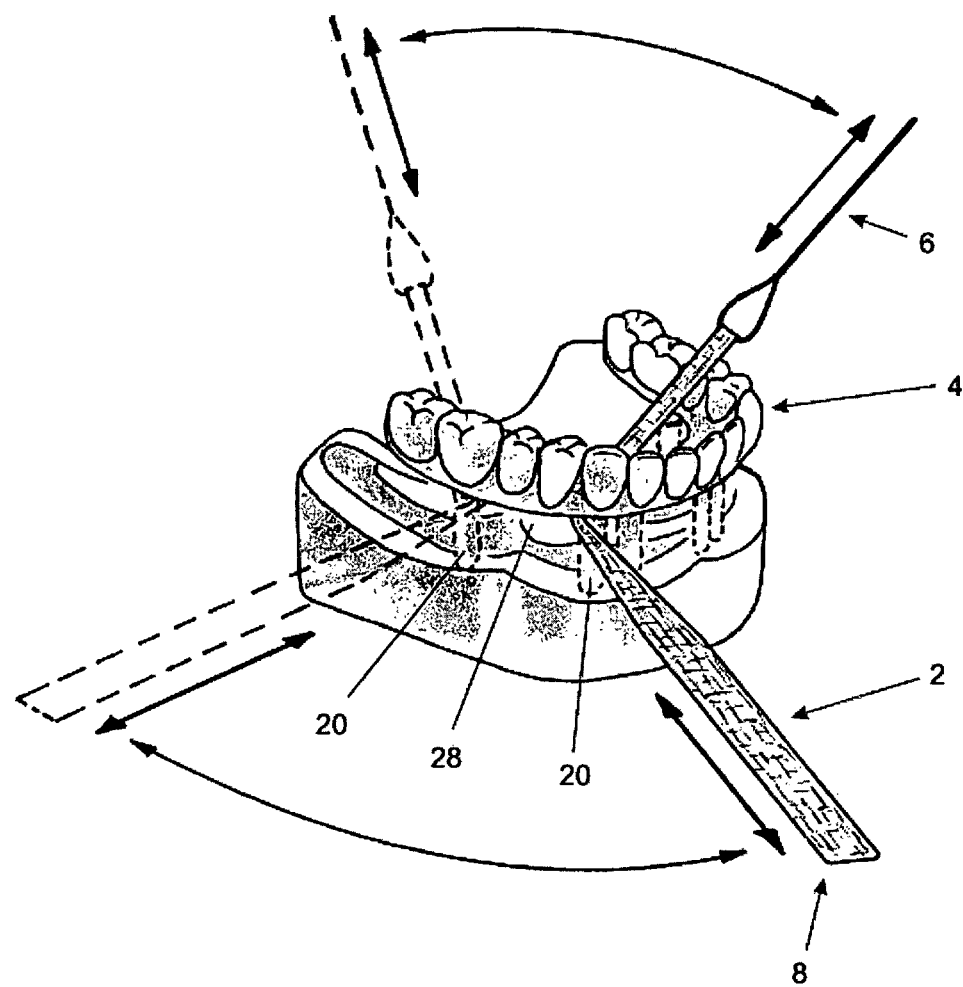
FIG. 5 shows a dental prosthesis being cleaned with a follower of the dental cleaning aid of FIG. 1.

According to an embodiment of the present invention, there is provided a disposable dental cleaning aid 2 as shown in FIGS. 1 to 3. The dental cleaning aid 2 is suitable for cleaning a dental prosthesis 4 as shown in FIGS. 4 and 5, or for cleaning any wide inter-dental spaces which may be between natural teeth, crowns, bridges or implants.

Turning to FIG. 1, the aid 2 includes a threader (or leader) 6 formed from a monofilament and a cleaning follower 8 for following the threader 6. The leading portion 10 of the threader 6 is narrow to facilitate threading though gaps of the prosthesis 4 whereas the trailing portion 12 of the follower 8 is wide to facilitate cleaning in the gaps. As can best be seen in FIG. 3, the dental cleaning aid 2 includes a loop or fold fastening arrangement by which the threader 6 and follower 8 are fastened together. The aid 2 will be described in detail below.

With reference to FIG. 3, the threader 6 defines a loop 14 or fold through which the follower 8 passes. The monofilament forming the threader 6 is a single strand of nylon or other polymeric material fastened relative to itself to form the loop 14 behind the leading portion 10. The leading portion 10 of the threader 6 consisting of the folded monofilament is comparatively narrow and resistant to bending to facilitate threading through gaps to be cleaned.

The follower 8 defines a loop or fold 16 through which the threader 6 passes. The follower 8 is formed from a single strip or ribbon of material fastened relative to itself to form the loop 16. A number of spot welds 18 fastens the strip of material relative to itself. The follower material is gauze formed from soft non-woven fabric and is well adapted to engaging with food, debris or plaque owing to its inherently abrasive and absorbent characteristics. The gauze is moisture-absorbent and can be impregnated with flavored particles or an antibacterial agent. The follower 8 defines a tapered portion 20 proximal to the threader 6 to facilitate insertion of the follower 8 into a gap to be cleaned.

Turing to FIG. 4, the dental prosthesis 4 includes posts 20 embedded in a patient's lower jaw bone 22. A bridge 24 bearing artificial teeth 26 is supported by the posts 20, and a wide gap 28 to be cleaned is defined between the posts 20. During cleaning, the leading portion 10 of the threader 6 can be readily threaded though the wide gap 28 of the dental prosthesis 4.

Turing to FIG. 5, the follower 8 follows the threader 6 into the gap 28 between the posts 20 and is reciprocated to clean the gap 28. In practice, optimal cleaning would involve reciprocating the follower 8 against all surfaces forming the gap 28, including both posts 20 respectively. Advantageously, the aid 2 enables the patient to properly clean the dental prosthesis 4 without requiring the attendance of a dental professional.

A method for forming the dental cleaning aid 2 is now described. The method involves the step of fastening the threader 6 to the follower 8 using a loop or fold fastening arrangement. The loop or fold fastening arrangement is formed by fastening loops or folds of the threader 6 and follower 8 together as described below.

The method involves initially passing the follower 8 through the loop 14 of the threader 6. In turn, the follower 8 is fastened to itself to form another loop 16 through which the threader 6 passes. The follower 8 is fastened to itself by spot welding the follower 8. This method is simplistic and forms an effective joint between the threader 6 and follower 8.

The method may further involve the step of impregnating the follower 8 with flavored particles or an antibacterial agent.

Figure 6:
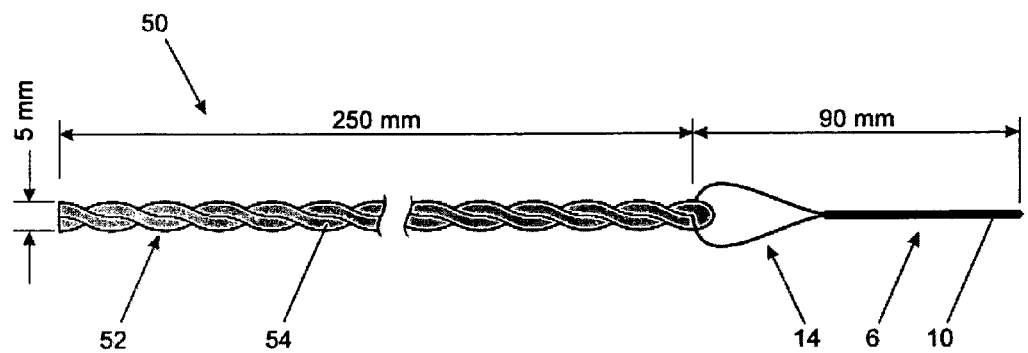
FIG. 6 is a plan view of a dental cleaning aid in accordance with a second embodiment of the present invention.
Figure 7:
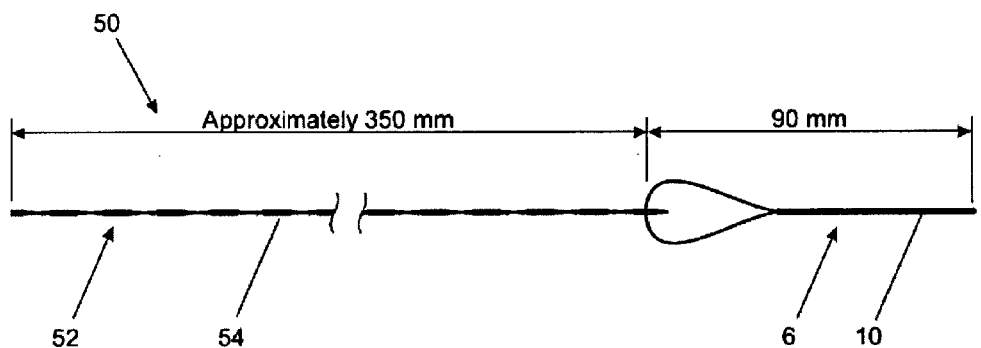
FIG. 7 is a plan view of the dental cleaning aid of FIG. 6 with a stretched follower.
Figure 8:
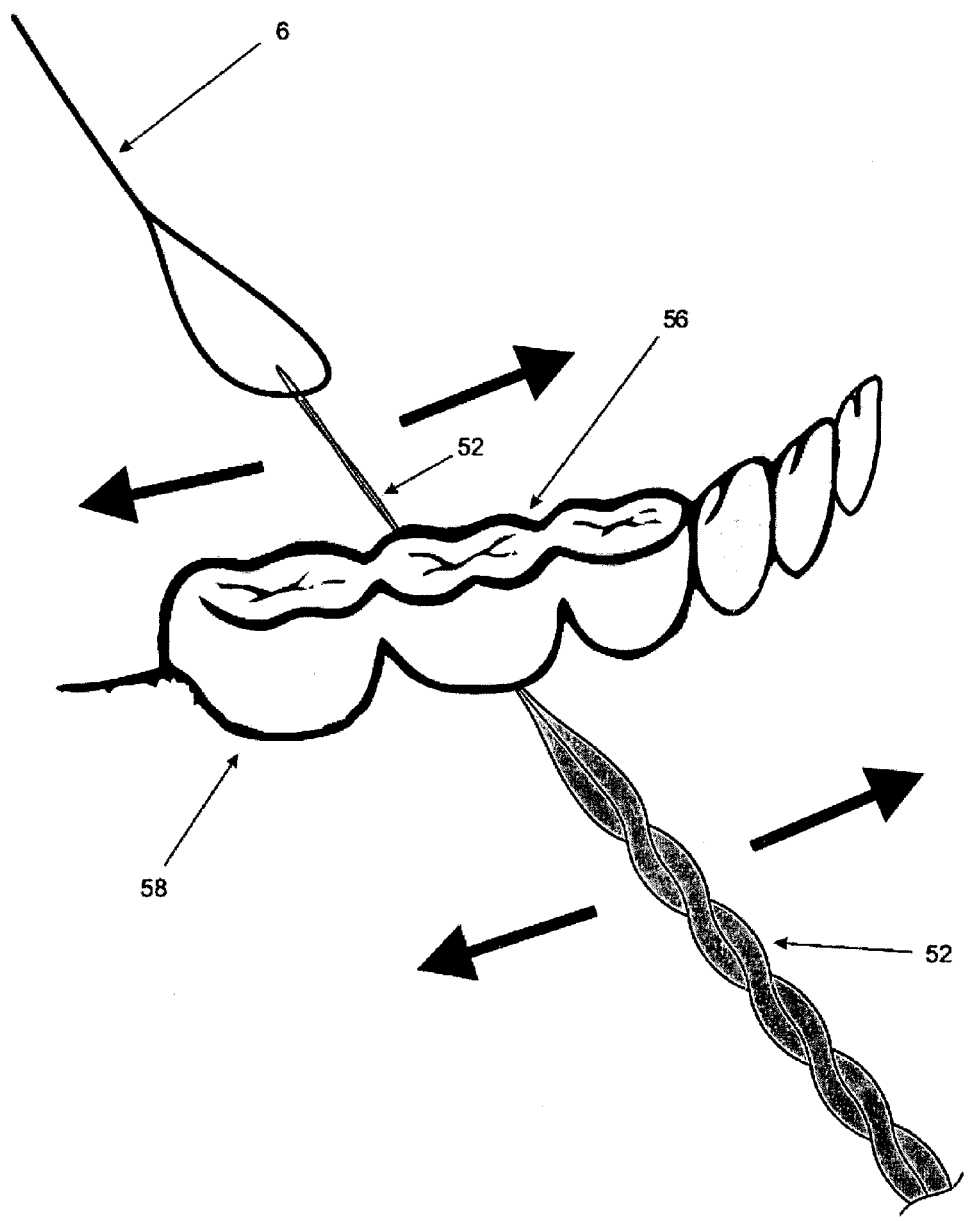
FIG. 8 shows a dental bridge being cleaned with the dental cleaning aid of FIG. 6.

According to another embodiment of the present invention, there is provided a disposable dental cleaning aid 50 as shown in FIGS. 6 to 8. Like reference numerals refer to like features previously described.

The cleaning aid 50 includes a follower 52 which is engaged with the threader 6 using a loop or fold fastening arrangement. The follower 52 consists of a folded and twisted length of nylon material 54. The follower 52 is resiliently stretchable, and can be stretched from its resting length shown in FIG. 6 to about 1.4 times its resting length as shown in FIG. 7. As can best be seen in FIG. 7, the follower 52 can be stretched to be of comparable width as the leading portion 10 of the threader 6. Fastening of the follower 52 and loop 14 is achieved without gluing, welding knotting, crimping or like joining of the folded follower to itself.

The nylon material 54 is a multi-strand nylon yarn, namely texturized nylon 6.0 or 6.6 yarn. The nylon yarn consists of six plies of a 300 denier (333 dtex) texturized nylon yarn. The yarn may have 68 filaments per ply. The final strand may be 1800 denier (2000 dtex) with a filament count of 408.

Turning to FIG. 8, the threader 6 can be initially fed between a tooth bridge 56 and gum 58. The follower 52 is stretched when passing between the bridge 56 and gum 58, and can be moved laterally to clean beneath the bridge 56.

When forming the dental cleaning aid 50, the threader 6 and follower 52 are fastened together. The fastening involves folding the follower 52 to receive a loop 14 of the threader 6. The follower 52 is then twisted to contain the loop 14 within the follower 52. The twisted follower 52 may be coated with a microcrystalline wax, flavorants, colourants, or an antibacterial agent.

A person skilled in the art will appreciate that many embodiments and variations can be made without departing from the ambit of the present invention.

In one embodiment, the threader 6 is injection molded from thermoplastic material as a single piece including the loop 14 and the leading portion 10.

In another embodiment, the step of fastening the threader 6 to the follower 8 instead involves the steps of:

passing the threader 6 through the loop 16 of the follower 8; and fastening the threader 6 to itself to form another loop 14 through which the follower 8 passes. The threader 6 is fastened to itself by heat welding the threader 6.

The dimensions of the dental cleaning aid 2 shown in the Figures are in millimetres, and are by way of example only.

Alternative embodiments of the invention may involve fastening the threader 6 directly onto the fabric of the follower 8 without a loop arrangement, by instead thermal welding, gluing or stitching the threader 6 and the follower 8 together.

In one embodiment, the ribbon like follower 8 may include two adjacent layers of fabric, instead of one layer.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims appropriately interpreted by those skilled in the art.

The invention claimed is:

1. A dental cleaning aid including:
   a threader being a looped monofilament fastened to itself, wherein a leading portion of the threader is resistant to bending; and
   a follower following the threader and being at least in part wider than the monofilament, the follower being a looped length of material twisted to form a double helix, the material when unlooped having a greater cross sectional area than the monofilament;
   wherein the follower passes through the looped monofilament of the threader and is twisted together with itself to secure the looped length of material of the follower to the looped monofilament of the threader.

2. A dental cleaning aid as claimed in claim 1, wherein the leading portion of the threader is fine to facilitate threading though gaps whereas a trailing portion of the follower is wide to facilitate cleaning in the gaps.

3. A dental cleaning aid as claimed in claim 1, wherein the monofilament is a single strand of nylon or other polymeric material.

4. A dental cleaning aid as claimed in claim 1, wherein the material is a multi-strand nylon yarn.

5. A dental cleaning aid as claimed in claim 1, wherein the follower is resiliently stretchable.

6. A dental cleaning aid as claimed in claim 1, wherein the follower can be stretched up to about 1.4 times its resting length.

7. A dental cleaning aid as claimed in claim 1, wherein the follower can be stretched so as to be of comparable width as the leading portion of the threader.

8. A dental cleaning aid as claimed in claim 1, wherein the follower is moisture-absorbent and impregnated with colored or flavored particles, or an antibacterial agent.

9. A method for forming a dental cleaning aid, the method involving the step of fastening a threader, being a looped monofilament fastened to itself, to a follower being at least in part wider than the monofilament, the step of fastening involving looping and twisting the follower to form a double helix that contains the looped monofilament of the threader within the looped follower, the unlooped follower having a greater cross sectional area than a monofilament, wherein a leading portion of the threader is resistant to bending.

10. A method as claimed in claim 9, further including the step of applying to the follower one or more of a wax, flavorants, colourants, and an antibacterial agent.

* * * * *